United States Patent [19]

Hartman et al.

[11] 4,010,173

[45] Mar. 1, 1977

[54] SYNTHESIS OF 4-CYANOTHIAZOLES

[75] Inventors: George D. Hartman, Plainsboro; Leonard M. Weinstock, Belle Mead, both of N.J.

[73] Assignee: Merck & Co., Inc., Rahway, N.J.

[22] Filed: Feb. 26, 1975

[21] Appl. No.: 553,185

[52] U.S. Cl. ............................................ 260/302 R
[51] Int. Cl.² ....................................... C07D 277/28
[58] Field of Search ................................ 260/302 R

[56] References Cited

UNITED STATES PATENTS 3,476,766  11/1969  Brown et al. .................. 260/302 R
3,769,040  10/1973  Pittet et al. ..................... 260/302 R

*Primary Examiner*—Nicholas S. Rizzo
*Assistant Examiner*—D. B. Springer
*Attorney, Agent, or Firm*—Donald J. Perrella; J. Jerome Behan

[57] ABSTRACT

4-Cyanothiazoles are prepared by reacting $\beta,\beta$-dichloro-$\alpha$-amino-acrylonitrile with a thioformamide in the presence of an acidic catalyst.

9 Claims, No Drawings

SYNTHESIS OF 4-CYANOTHIAZOLES

BACKGROUND OF THE INVENTION

The present invention relates to the synthesis of 4-cyanothiazoles. More particularly, it relates to a one-step synthesis which reacts $\beta,\beta$-dichloro-$\alpha$-aminoacrylonitrile with a thioformamide in the presence of an acidic catalyst.

4-Cyanothiazoles are intermediates for the synthesis of thiabendazole, 2-(4-thiazolyl)benzimidazole and related compounds. A simple, one-step synthesis for 4-cyanothiazoles, however, has not heretofore been available. It is, accordingly, an object of the present invention to provide an improved synthesis for the preparation of 4-cyanothiazoles. A further object is to provide a simple, one-step synthesis for 4-cyanothiazoles. A further object is to provide a shorter synthesis for thiabendazole starting from a 4-cyanothiazole precursor. These and other objects of the present invention will be apparent from the following description.

SUMMARY OF THE INVENTION

4-Cyanothiazoles are prepared by reacting $\beta,\beta$-dichloro-$\alpha$-amino-acrylonitrile with a thioformamide in the presence of an acidic catalyst.

DETAILED DESCRIPTION

The synthesis and use of thiabendazole, 2-(4-thiazolyl)benzimidazole and related compounds, is described in U.S. Pat. No. 3,017,415. These compounds find application in veterinary use, as broad spectrum anthelminitics and fungicides. They are particularly useful in treatment of ringworm in cattle. The synthesis of thiabendazole and related compounds starting from 4-cyanothiazole or an R-substituted 4-cyanothiazole proceeds according to the sequence

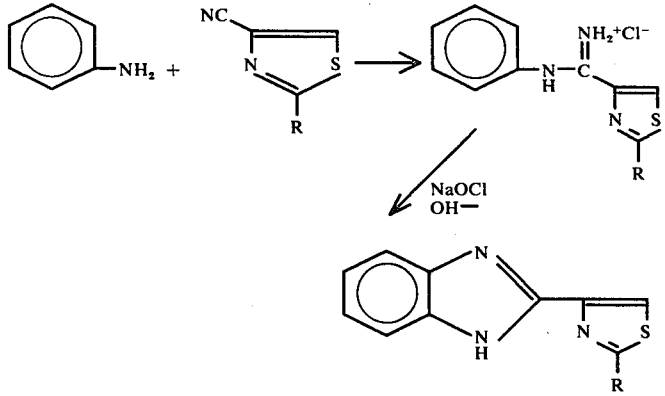

The conditions for the foregoing reaction are those described by Grenda et al., J. Org. Chem. 30, 259 (1965): A simple, one-step synthesis for the 4-cyanothiazole intermediates would greatly simplify and shorten the preparation of thiabendazole and related compounds.

It has now been found that 4-cyanothiazoles may be prepared in one step by reacting $\beta,\beta$-dichloro-$\alpha$-aminoacrylonitrile with a thioformamide in the presence of an acidic catalyst. The reaction takes place in a polar organic solvent such as, for example, acetone, or acetonitrile at temperatures of from about 45° to about 90° for a period of from about 1 to about 10 hours, preferably for from about 2 to about 7 hours. The acidic catalyst may be, for example, hydrochloric, sulfuric or p-toluenesulfonic acid. The thioformamide is preferably present in excess amount, generally in a molar amount about twice that of the $\beta,\beta$-dichloro-$\alpha$-aminoacrylonitrile. The reaction sequence is as follows:

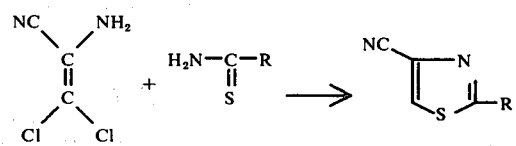

In the foregoing equations, the R-substituent may be hydrogen, straight or branched, alkyl of from 1 to 10 carbons, phenyl alkyl wherein the alkyl group is from 1 to 10 carbon atoms, phenyl or phenyl substituted by methyl, halogen or nitro.

The following examples illustrate the present invention without, however, limiting the same thereto. All temperatures are expressed in degrees Celsius unless stated otherwise.

EXAMPLE 1

4-Cyanothiazole

A round bottom flask is charged with 10.0 g. (0.16 mole) of thioformamide, 11.2 g. (0.08 mole) of $\beta,\beta$-dichloro-$\alpha$-aminoacrylonitrile, 0.83 g. (0.004 mole) of p-toluenesulfonic acid monohydrate and 300 ml. of acetone. The resulting yellow solution is heated at reflux with magnetic stirring for three hours. As the reaction progresses a yellow precipitate appears on the sides of the flask. After the heating period is completed, the reaction solution is cooled and then filtered through a sintered glass funnel to give a clear yellow solution. This solution is stripped on the rotary evaporator and the residue is recrystallized from hexane to give 4-cyanothiazole as white crystals, m.p. 55°–56°.

EXAMPLE 2

2-Methyl-4-cyanothiazole

A round-bottom flask is charged with 3.0 g. (0.02 mole) of β,β-dichloro-α-aminoacrylonitrile, 3.30 g. (0.04 mole) of thioacetamide, 0.23 g. (0.0011 mole) of p-toluenesulfonic acid monohydrate and 100 ml. of acetonitrile. A condenser is attached to the flask and the reaction solution is heated at 70° for 5 hours. After this time the solution is considerably darkened and the starting olefin has been consumed. The reaction solution is cooled and then decolorized with activated carbon and filtered through a sintered glass funnel. The resulting clear solution is then distilled to give 2-methyl-4-cyanothiazole as a clear liquid, b.p. 137°/25mm, which upon cooling crystallizes, m.p. 59°–61°.

EXAMPLES 3–11

Following the procedure of Example 2, but substituting an equimolar amount of the thiobenzamide compound listed below in column I, for thioacetamide, the corresponding substituted-4-cyanothiazole compound listed in Column II is prepared.

| Example | I | II |
|---|---|---|
| 3 | thiobenzamide | 2-phenyl-4-cyanothiazole |
| 4 | 2-methylthiobenzamide | 2-(2'-methylphenyl)-4-cyanothiazole |
| 5 | 3-methylthiobenzamide | 2-(3'-methylphenyl)-4-cyanothiazole |
| 6 | 4-methylthiobenzamide | 2-(4'-methylphenyl)-4-cyanothiazole |
| 7 | 3-bromothiobenzamide | 2-(3'-bromophenyl)-4-cyanothiazole |
| 8 | 4-chlorothiobenzamide | 2-(4'-chlorophenyl)-4-cyanothiazole |
| 9 | 4-iodothiobenzamide | 2-(4'-iodophenyl)-4-cyanothiazole |
| 10 | 3-nitrothiobenzamide | 2-(3'-nitrophenyl)-4-cyanothiazole |
| 11 | 4-nitrothiobenzamide | 2-(4'nitrophenyl)-4-cyanothiazole |
| 12 | phenylthioacetamide | 2-benzyl-4-cyanothiazole |

What is claimed is:

1. A method for the synthesis of a 4-cyanothiazole which comprises reacting in the presence of an acidic catalyst β,β-dichloro-α-amino-acrylonitrile with a compound of the formula

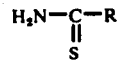

wherein R is hydrogen, straight or branched alkyl of form 1 to 10 carbon atoms, phenyl alkyl wherein the alkyl group is from 1 to 10 carbon atoms, phenyl or substituted phenyl wherein the substituent is methyl, F, Cl, Br, I or nitro, the acidic catalyst being hydrochloric acid, sulfuric acid or p-toluene-sulfonic acid.

2. A method according to claim 1 wherein R is hydrogen.

3. A method according to claim 1 wherein R is methyl.

4. A method according to claim 1 wherein the compound of the formula

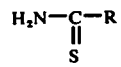

is present in excess amount.

5. A method according to claim 1 wherein the reaction takes place in a polar organic solvent.

6. A method according to claim 5 wherein the polar organic solvent is acetone or acetonitrile.

7. A method according to claim 1 wherein the reaction takes place at a temperature of from about 45° to about 90° C.

8. A method according to claim 1 wherein the reaction is used in the presence of a polar organic solvent at a temperature of from about 45° to about 90° C. for a period of from about 1 to about 10 hours and wherein the compound of the formula

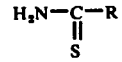

is present in molar excess relative to the molar quantity of β,β-dichloro-α-amino-acrylonitrile.

9. A method according to claim 8 wherein R is hydrogen or methyl.

* * * * *